United States Patent
Fargo et al.

(10) Patent No.: US 9,423,369 B2
(45) Date of Patent: Aug. 23, 2016

(54) RESISTANCE-BASED MONITORING SYSTEM AND METHOD

(75) Inventors: Richard N. Fargo, Plainville, CT (US); Peter Keyo, Canton, CT (US)

(73) Assignee: OTIS ELEVATOR COMPANY, Farmington, CT (US)

( * ) Notice: Subject to any disclaimer, the term of this patent is extended or adjusted under 35 U.S.C. 154(b) by 170 days.

(21) Appl. No.: 13/820,387

(22) PCT Filed: Sep. 1, 2010

(86) PCT No.: PCT/US2010/047445
§ 371 (c)(1),
(2), (4) Date: Mar. 1, 2013

(87) PCT Pub. No.: WO2012/030332
PCT Pub. Date: Mar. 8, 2012

(65) Prior Publication Data
US 2013/0162266 A1  Jun. 27, 2013

(51) Int. Cl.
*G01R 27/14* (2006.01)
*G01N 27/20* (2006.01)
*B66B 7/12* (2006.01)
*D07B 1/14* (2006.01)

(52) U.S. Cl.
CPC .............. *G01N 27/20* (2013.01); *B66B 7/1223* (2013.01); *D07B 1/145* (2013.01)

(58) Field of Classification Search
CPC ...................................................... G01R 27/14
See application file for complete search history.

(56) References Cited

U.S. PATENT DOCUMENTS

| | | | |
|---|---|---|---|
| 5,307,672 A * | 5/1994 | Macchiarulo et al. | ..... 73/114.77 |
| 5,834,942 A | 11/1998 | De Angelis | |
| 5,886,308 A | 3/1999 | Ericson et al. | |
| 5,890,564 A | 4/1999 | Olsen et al. | |
| 5,992,574 A | 11/1999 | Olsen et al. | |
| 6,073,728 A | 6/2000 | Olsen et al. | |
| 6,082,122 A * | 7/2000 | Madenokouji et al. | ........... 62/77 |

(Continued)

FOREIGN PATENT DOCUMENTS

| | | |
|---|---|---|
| CN | 1351710 A | 5/2002 |
| CN | 1433372 A | 7/2003 |

(Continued)

OTHER PUBLICATIONS

Japanese Office Action, Application No. 2013/527047 dated on Apr. 16, 2014.

(Continued)

*Primary Examiner* — Tung X Nguyen
*Assistant Examiner* — Feba Pothen
(74) *Attorney, Agent, or Firm* — Cantor Colburn LLP

(57) ABSTRACT

A monitoring system for a support structure is provided. The monitoring system may include a resistance circuit coupled to the support structure, and an interface circuit coupled to the resistance circuit. The resistance circuit may include a first set of resistors and a second set of resistors, wherein the second set of resistors is configured to provide a reference voltage. The interface circuit may include one or more comparators, wherein each comparator is configured to compare a voltage across at least one of the resistors with the reference voltage and generate an output signal corresponding to the comparison. The interface circuit may be configured to continuously monitor an effective resistance of the support structure based on the output signals.

17 Claims, 5 Drawing Sheets

(56) References Cited

U.S. PATENT DOCUMENTS

| | | | |
|---|---|---|---|
| 6,123,176 A | 9/2000 | O'Donnell et al. | |
| 6,289,742 B1 | 9/2001 | De Angelis | |
| 6,422,088 B1 * | 7/2002 | Oba et al. | 73/754 |
| 6,633,159 B1 | 10/2003 | Robar et al. | |
| 6,653,943 B2 | 11/2003 | Lamb et al. | |
| 6,684,981 B2 | 2/2004 | Stucky et al. | |
| 6,886,666 B2 | 5/2005 | Stucky et al. | |
| 6,943,576 B2 * | 9/2005 | Byun et al. | 324/762.03 |
| 7,117,981 B2 | 10/2006 | Logan et al. | |
| 7,123,030 B2 | 10/2006 | Robar et al. | |
| 7,409,870 B2 | 8/2008 | Stucky et al. | |
| 7,410,033 B2 | 8/2008 | Veronesi et al. | |
| 7,506,728 B2 | 3/2009 | Hawkes et al. | |
| 7,540,359 B2 | 6/2009 | Veronesi et al. | |
| 8,337,082 B2 * | 12/2012 | Coursey et al. | 374/185 |
| 8,813,918 B2 * | 8/2014 | Kocher et al. | 187/391 |
| 2002/0194935 A1 | 12/2002 | Clarke et al. | |
| 2003/0124417 A1 * | 7/2003 | Bertness et al. | 429/90 |
| 2004/0046540 A1 | 3/2004 | Robar et al. | |
| 2004/0053695 A1 | 3/2004 | Mattice et al. | |
| 2005/0116910 A1 | 6/2005 | Lee | |
| 2007/0168159 A1 | 7/2007 | Veronesi et al. | |
| 2007/0170012 A1 | 7/2007 | Stucky | |
| 2007/0181385 A1 | 8/2007 | Veronesi et al. | |
| 2008/0202863 A1 | 8/2008 | Rossignol et al. | |
| 2008/0223668 A1 | 9/2008 | Stucky et al. | |

FOREIGN PATENT DOCUMENTS

| | | |
|---|---|---|
| CN | 101263073 A | 9/2008 |
| EP | 1357073 A1 | 10/2003 |
| EP | 1362001 B1 | 2/2006 |
| EP | 2172410 A2 | 7/2010 |
| JP | 62146889 A | 6/1987 |
| JP | H06286957 A | 10/1994 |
| JP | 06286957 | 11/1994 |
| JP | H1179589 A | 3/1999 |
| JP | 2002/348068 A | 12/2002 |
| JP | 2009/132482 | 6/2009 |
| JP | 2009/143678 A | 7/2009 |
| KR | 10-2006-0097072 A | 9/2006 |
| KR | 100846944 B1 | 7/2008 |
| WO | WO 00/58706 A2 | 10/2000 |
| WO | WO 02/46082 A1 | 6/2002 |
| WO | WO 02/062695 A1 | 8/2002 |
| WO | WO 2005/094248 A2 | 10/2005 |
| WO | WO 2005/095250 A1 | 10/2005 |
| WO | WO 2005/097651 A2 | 10/2005 |
| WO | WO 2008/140520 A1 | 11/2008 |

OTHER PUBLICATIONS

Korean Office Action, Application No. 10-2013-7008134 dated Apr. 26, 2014.

Chinese Office Action, Application No. 201080068855.8 dated on Sep. 1, 2014.

International Search Report and Written Opinion for related Internatioanl Application No. PCT/US2010/047445 dated May 30, 2011, 3 pages.

* cited by examiner

| Output Node | Operational State | Thresholds | Interface Output |
|---|---|---|---|
| 44g | [Reference] | [--] | [--] |
| 44f | Shorted State | V(44f) > V(44g) | Alarm / Red LED |
| 44e | Normal State | V(44e) < V(44g) | Green LED |
| 44d | Normal State | V(44d) > V(44g) | Green LED |
| 44c | Low-wear State | V(44c) < V(44g) | Yellow LED |
| 44b | End-of-life State | V(44b) < V(44g) | Alarm / Red LED |
| 44a | Open-circuit or High-wear State | V(44a) < V(44g) | Alarm / Red LED |

RESISTANCE-BASED MONITORING SYSTEM AND METHOD

CROSS-REFERENCE TO RELATED APPLICATIONS

This application is a U.S. national stage filing under 35 USC §371 of International Patent Application No. PCT/US10/47445, filed on Sep. 1, 2010.

FIELD OF THE DISCLOSURE

The present disclosure generally relates to monitoring systems and methods, and more particularly, to systems and methods for monitoring the condition of a support structure, for example a belt used in an elevator system.

BACKGROUND OF THE DISCLOSURE

Tensile support structures, such as coated steel belts or wire ropes containing metal cords, are used to move an elevator car up and down within an elevator shaft or hoistway. Because the condition of the tensile support structure is critical to the safety of the operation of the elevator, there is a need to determine the remaining strength level of the tensile support and detect if the remaining strength level falls below a minimum threshold.

The strength of a tensile support structure can be reduced by normal operation of the elevator over time. The primary source of the degradation in the strength of the support structure is the cyclic bending of the support structure around sheaves as the elevator is moved up and down in an elevator shaft or hoistway. The degradation of a support structure is normally not uniform along the length of the support structure, but rather, focused to areas of the support structure that are subjected to high levels or severities of bending cycles.

Some electrical characteristics, such as electrical resistance or impedance, of the cables, cords or tension members in the support structure will vary as the cross-sectional areas of the tension members decrease. Accordingly, it is possible to determine the remaining support strength of the support structure based on the electrical characteristics of the tension members thereof. There currently are some monitoring systems which employ a resistance-based inspection scheme to monitor the resistance of support structures, and thus, the remaining strength thereof. Such systems are built upon microprocessor based designs, which utilize several analog to digital and/or digital to analog interfaces, and other added implementations for processing digital signals. The digital nature of such systems further rely on sampled data, and thus, are unable to provide continuous monitoring or immediate responses to detected fault conditions.

Accordingly, there is a need for a system and method for monitoring that is less complex and more cost-effective. Alternatively or in addition, there is a need for systems and methods that are capable of providing continuous monitoring of support structures and immediate response to detected fault conditions. Finally, there is an alternative or additional need for a monitoring system that allows for easier and more accurate calibrations thereof.

SUMMARY OF THE DISCLOSURE

In accordance with one aspect of the disclosure, a monitoring system for a support structure is provided. The monitoring system may include a resistance circuit coupled to the support structure, and an interface circuit coupled to the resistance circuit. The resistance circuit may have a first set of resistors and a second set of resistors, wherein the second set of resistors is configured to provide a reference voltage. The interface circuit may include one or more comparators, wherein each comparator is configured to compare a voltage across at least one of the resistors with the reference voltage and generate an output signal corresponding to the comparison. The interface circuit may be configured to continuously monitor an effective resistance of the support structure based on the output signals.

In accordance with another aspect of the disclosure, a method for calibrating a resistance-based monitoring system for a support structure is provided. The method may provide a resistance circuit coupled to the support structure, wherein the resistance circuit includes a first set of resistors and a second set of resistors disposed at least partially in parallel to the support structure. The method may further generate a reference voltage across the second set of resistors, compare a voltage across at least one of the first set of resistors with the reference voltage, and adjust the reference voltage until an effective resistance of the support structure is substantially matched by the resistance circuit.

In accordance with yet another aspect of the disclosure, a method for monitoring a support structure is provided. The method may provide a resistance circuit coupled to the support structure, wherein the resistance circuit includes a first set of resistors and a second set of resistors disposed at least partially in parallel to the support structure. The method may further generate a reference voltage across the second set of resistors, wherein the reference voltage corresponding to an initial effective resistance of the support structure. The method may also compare a voltage across at least one of the first set of resistors with the reference voltage, and determine at least one operational state of the support structure based on the comparisons.

These and other aspects of this disclosure will become more readily apparent upon reading the following detailed description when taken in conjunction with the accompanying drawings.

Figure 1:
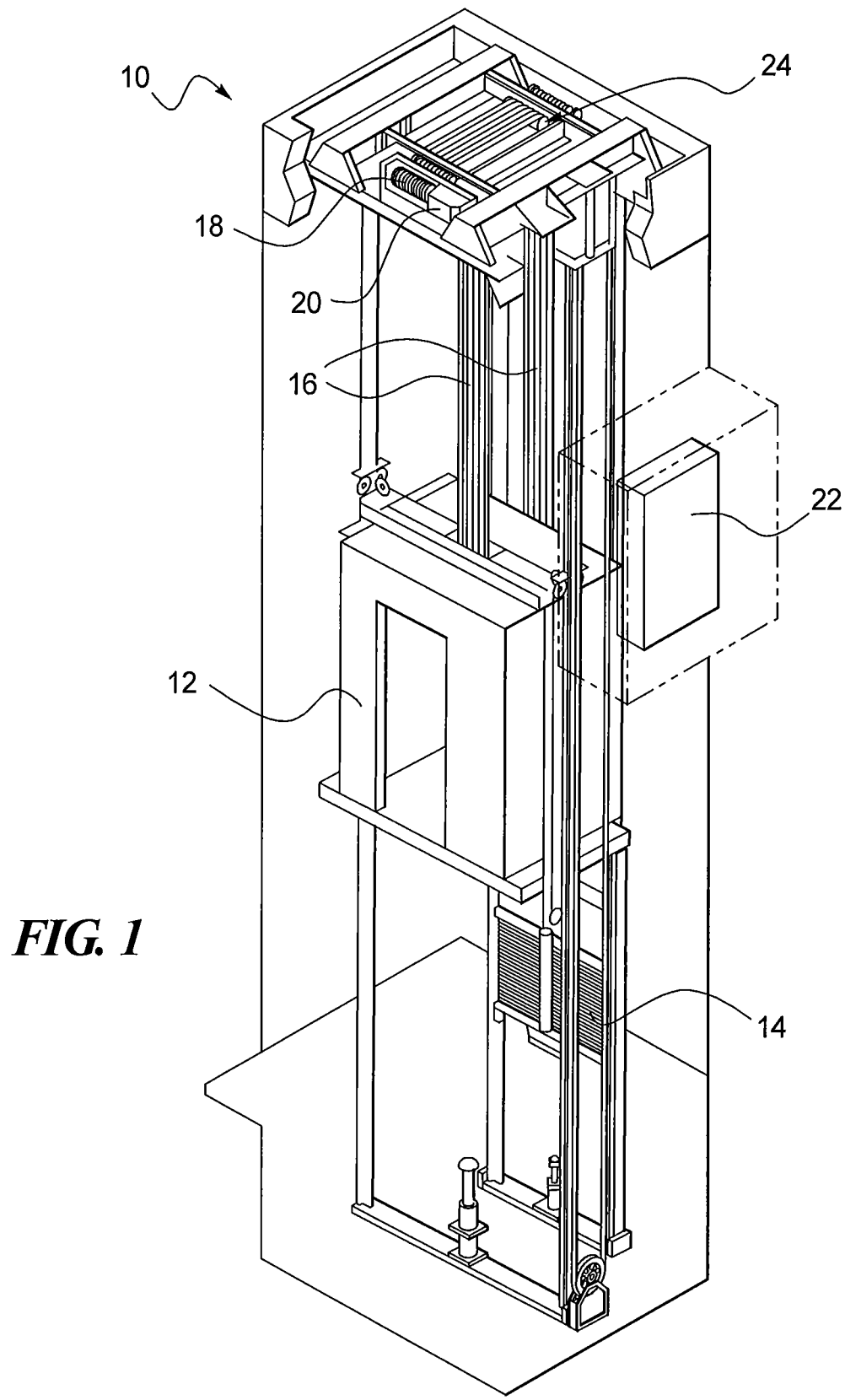
FIG. 1 is a partial perspective view of an elevator system.

While the present disclosure is susceptible to various modifications and alternative constructions, certain illustrative embodiments thereof have been shown in the drawings and will be described below in detail. It should be understood, however, that there is no intention to be limited to the specific forms disclosed, but on the contrary, the intention is to cover all modifications, alternative constructions, and equivalents falling with the spirit and scope of the present disclosure.

DETAILED DESCRIPTION

The present invention relates to monitoring of support structures. While FIG. 1 describes one possible support structure, in particular a tensile support structure, namely belts or ropes used to suspend and/or drive components of an elevator system, the present invention could be used with other support structures. Other exemplary support structures include belts or jacketed cords as used in exercise machines, jacketed cables as used with cranes, or any other multi-strand wire or rope being used in tension. Referring now to FIG. 1, an elevator system 10 is shown in schematic fashion. It is to be understood that the version of the elevator system 10 shown in FIG. 1 is for illustrative purposes only and to present background for the various components of a general elevator system.

As shown in FIG. 1, the elevator system 10 may include a car 12 coupled to a counterweight 14 by a support structure 16. The support structure 16 may extend over a traction sheave 18 that is driven by a machine 20. Traction between the sheave 18 and the support structure 16 may drive the car 12 and counterweight 14 through the hoistway. Operation of the machine 20 may be controlled by a main controller 22. The elevator system 10 may further include a monitoring system 24 in electrical communication with, and/or disposed in a location proximate to, the support structure 16 and configured to detect the condition of the support structure 16 by measuring, for example continuously or intermittently, the resistance thereof.

Figure 2A:
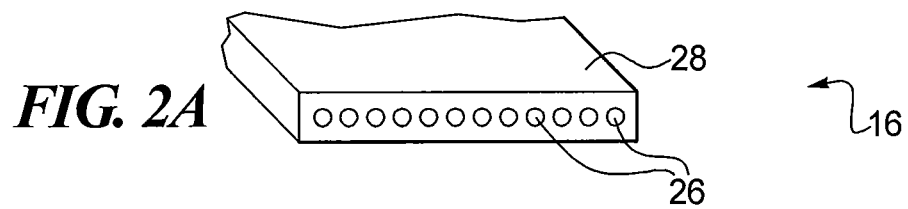
FIG. 2A is a partial perspective view of a tensile support structure.
Figure 2B:
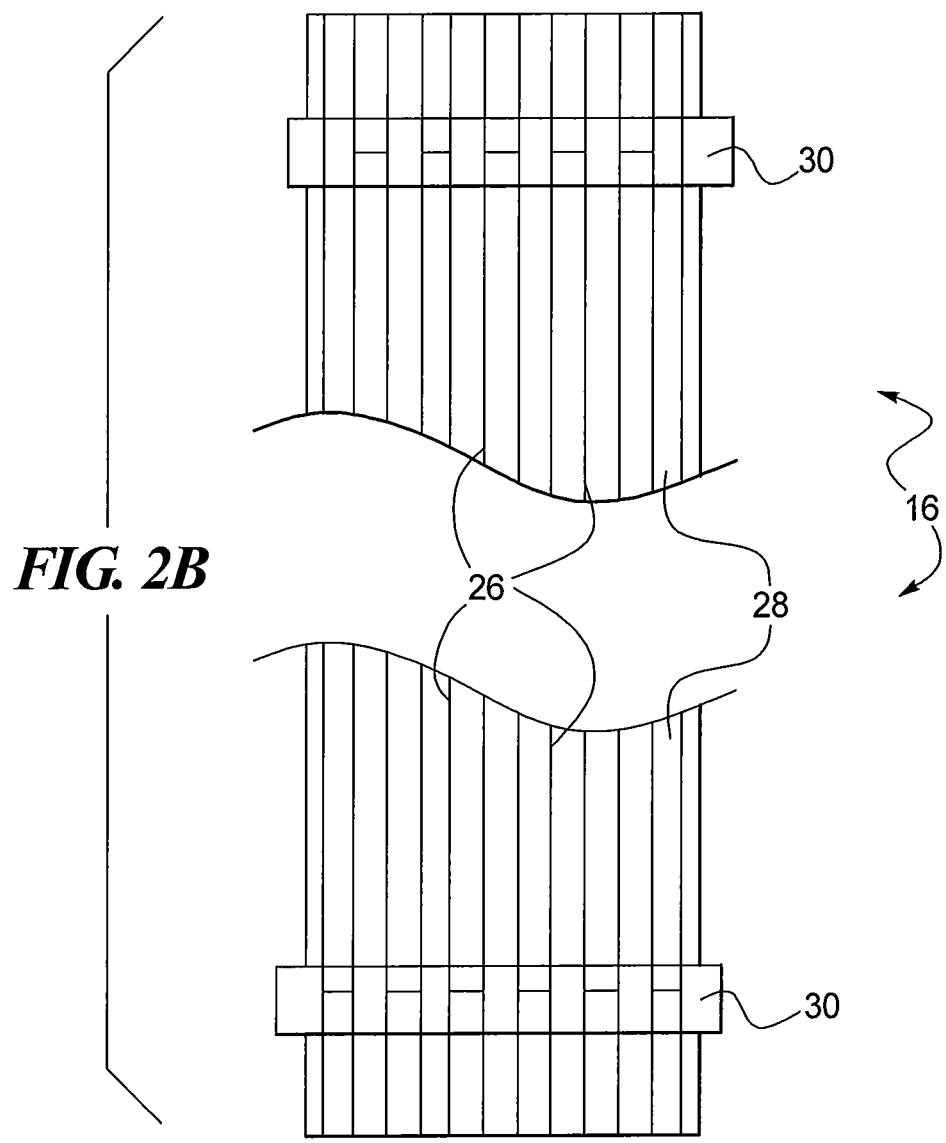
FIG. 2B is partial top plan view of two ends of a tensile support structure.

Turning to FIG. 2A, one exemplary support structure 16 is provided in the form of a belt having a plurality of individual tension members 26 in a jacket coating 28. The tension members 26 may include conventional steel wires formed into strands and/or cords, or any other supportive material having an electrical resistance. The jacket coating 28 may comprise one or more materials suitable for promoting traction with the traction sheave 18, such as polyurethane or elastomeric materials. The jacket coating 28 may additionally comprise an electrically insulative material suitable for prohibiting electrical communication therein. The operational condition or state of one or more (including each) tension member 26 of the support structure 16 of FIG. 2A may be determined using a resistance-based inspection scheme, wherein, for example, the remaining life of the one or more tension members 26 of the support structure 16 may be determined in terms of the increase in the resistance of the tension members 26 relative to a baseline value (for example measured during initial installation of the support structure 16 in the elevator system 10. The overall operational condition or state of a support structure 16 could be monitored continuously or intermittently for any substantial increase in resistance. The support structure 16 may also be monitored for any wear in the jacket coating 28 by, for example, detecting for any contact or electrical short between exposed tension members 26 and electrically conductive idler or traction sheaves 18. In one possible arrangement, the individual tension members 26 may be connected in series so as to minimize the number of monitored resistances and provide one effective resistance per support structure 16. The effective resistance of a support structure 16 may be indicative of the actual resistance, or any multiple, fraction or scale thereof, exhibited by the support structure 16. As shown by the ends of an exemplary support structure 16 of FIG. 2B, the tension members 26 may be coupled or shorted together at alternating and respective ends using connectors 30 so as to electrically connect the tension members 26 associated with one support structure 16 in series form. Other arrangements, such as monitoring one or more tension members 26 in parallel or a combination of parallel and serial monitoring of subsets of the tension members 26, are also possible.

Figure 3:
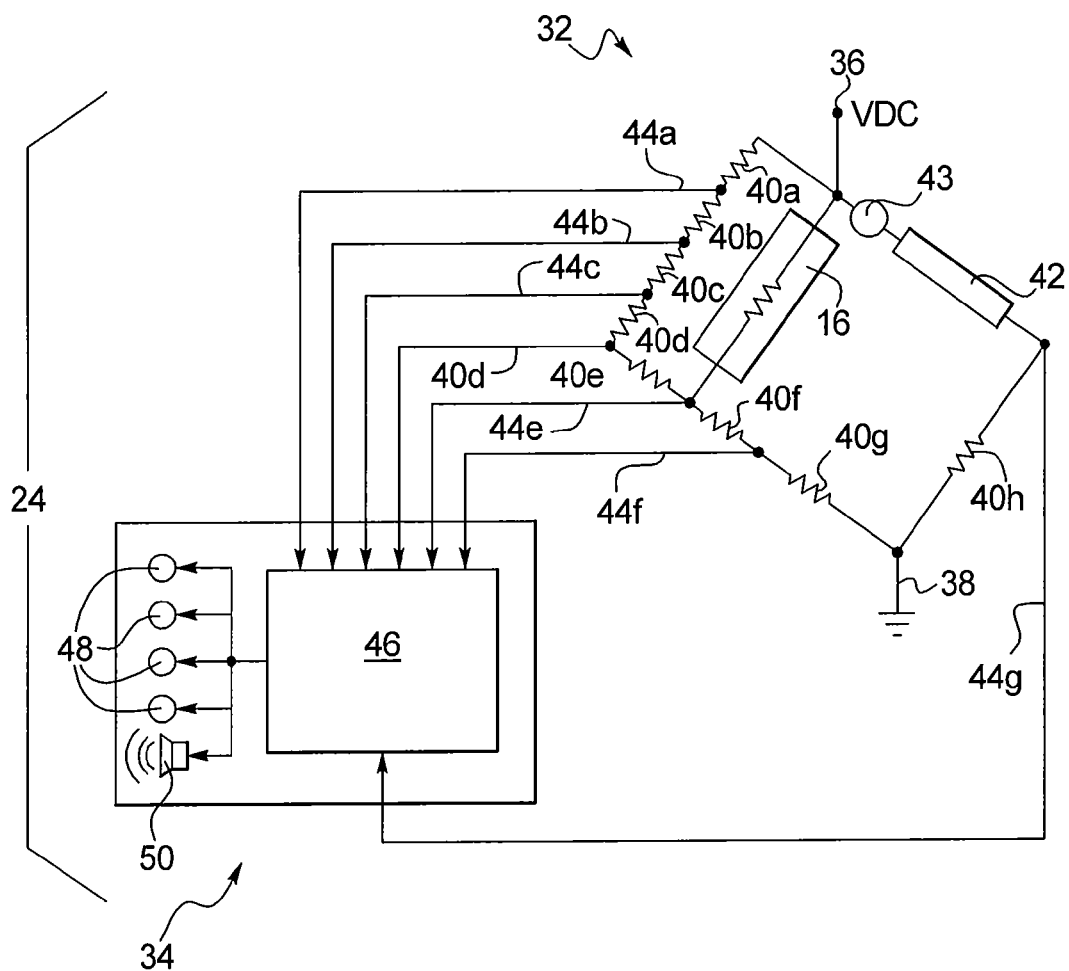
FIG. 3 is a schematic view of an exemplary monitoring system.

Referring now to FIG. 3, an exemplary system 24 for monitoring the wear condition of a support structure 16 of an elevator system 10 is provided. While other configurations may exist, the monitoring system 24 of FIG. 3 may include a resistance circuit 32 and an interface circuit 34 which employ a resistance-based inspection scheme. The monitoring system 24 may supply an electrical signal through the one or more tension members 26 of a support structure 16 and monitor for any changes in the electrical signal that may be indicative of an increase in resistance or wear. In the particular embodiment of FIG. 3, for example, the resistance circuit 32 may be configured to supply a direct current (DC) voltage across the support structure 16 and the interface circuit 34 may be configured to continuously monitor for changes in the electric current flowing through the support structure 16. Alternatively, the circuit 34 could intermittently monitor for changes in the electric current flowing through the support structure.

As shown in FIG. 3, the resistance circuit 32 may be configured to supply a voltage across the support structure 16 via a voltage input node 36 and a ground node 38 so as to induce an electrical current therethrough. The resistance circuit 32 may further provide a first set of resistors 40 as well as a second set of resistors 42 that are electrically coupled to the support structure 16 and generally arranged in a voltage divider configuration. For example, the first set of resistors 40 may provide output voltages at output nodes 44$a$-$f$ which gradually increase or decrease as the support structure 16 wears over time, while the second set of resistors 42 may provide a reference voltage at output node 44$g$ which remains constant until the next calibration. By comparing the output voltages provided by the first set of resistors 40 to the reference voltage provided by the second set of resistors 42, it may be possible to determine an operational condition or state of the support structure 16.

Still referring to the resistance circuit 32 of FIG. 3, resistors 40$a$-$e$ may be disposed in parallel to the support structure 16 while resistors 40$f$-$g$ may be disposed in series to resistors 40$a$-$e$ and the support structure 16. Resistors 40$a$-$e$ may be configured with relatively high resistances so as to minimize its effect on the current flowing through the support structure 16. Resistors 40$f$-$g$ may be disposed substantially parallel to resistor 40$h$, and further, configured to match the resistance thereof. Accordingly, the second set of resistors 42 may be configured to substantially match the effective resistance of the support structure 16, for example, during an initial calibration of the monitoring system 24, so as to provide the baseline or reference voltage to which the output voltages at output nodes 44$a$-$f$ may be compared. In alternative embodiments, the resistor circuit 32 may provide a reference voltage at output node 44$g$ using a pulse-width modulation (PWM) device, or any other suitable means for providing a reference voltage that can be set during calibration.

Figures 4, 5:
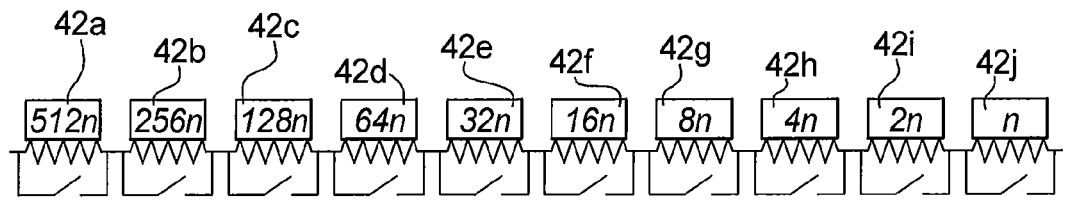
FIG. 4 is a schematic view of one exemplary set of adjustable resistors.
FIG. 5 is a tabular view of exemplary thresholds by which the monitoring system of FIG. 3 may operate.

As shown in FIG. 4, the second set of resistors 42 may employ a plurality of adjustable resistors 42$a$-$j$ having different, for example, successively increasing or decreasing, resistances that are each enabled by a dual in-line package (DIP) switch. By enabling or disabling each successive switch-enabled resistor 42$a$-$j$, an operator or inspector may be able to closely approximate and substantially match the effective resistance of the support structure 16 during the initial calibration. In the embodiment shown, the resistance of each adjacent resistor 42$a$-$j$ may be successively varied by a factor of two. Alternatively, the resistance of each adjustable resistor 42$a$-$j$ may be varied by a greater or lesser factor so as to provide a lower or higher resolution of detection, respectively. In other alternatives, the second set of resistors 42 may include a greater or lesser number of switch-enabled resistors 42 to vary the resolution of detection. In still further alternatives, the second set of resistors 42 may employ one or more potentiometers or any other combination of resistors with adjustable resistances. Once correctly calibrated, the resistance circuit 32 may be configured such that any change in the effective resistance of the support structure 16, and thus any wear thereof, will result in a change in the detected voltage across or current through any of the resistors 40a-h, 42. Optionally, one or more of the switch-enabled resistors 42 may be temporarily or permanently sealed upon calibration so as to prohibit any further change in the resistance thereafter. In further modifications, the second set of resistors 42 may employ one or more temperature-dependent resistors 43, such as resistive thermal devices (RTDs), or the like, having a resistance that varies with temperature so as to substantially match any change in the effective resistance of the support structure 16 caused by changes in temperature. Additionally or optionally, a temperature-dependent resistor 43 may be provided in series to the second set of resistors 42, as shown for example in FIG. 3.

Referring back to the monitoring system 24 of FIG. 3, the interface circuit 34 may be coupled to one or more output nodes 44a-g of the resistance circuit 32 and employ an analog approach to continuously monitor the effective resistance of the support structure 16. More specifically, using a series of comparators 46 and light emitting diodes (LEDs) 48, the interface circuit 34 may be configured to visually provide an operator or inspector with the corresponding operational state of the support structure 16 based on any detected change in the effective resistance thereof. A change in the effective resistance of the support structure 16 may be determined, for example, by comparing the magnitudes of one or more output voltage signals of the resistance circuit 32. Based on the degree of change detected in the effective resistance of the support structure 16, one or more preconfigured thresholds may be exceeded, and further, cause one or more LEDs 48 to illuminate and/or change the color thereof according to the table of FIG. 5. Furthermore, each comparator 46 may be coupled directly to a respective LED 48 so as to immediately illuminate the LED 48 in response to an enabling condition without the involvement of a microcontroller, microprocessor, or the like. Alternatively, a plurality of the outputs of the comparators 46 may be coupled to a single LED 48 via a switched or multiplexed connection.

According to the configuration provided in FIG. 5, one or more comparators 48 may compare the respective output voltage signals at the output nodes 44a-f of the resistance circuit 32 with a reference voltage signal at the output node 44g of, for example, the calibrated second set of resistors 42. As the support structure 16 wears, the effective resistance thereof may increase, and thus, in the resistor circuit 32 of FIG. 3, cause the voltages at output nodes 44a-d to decrease. Accordingly, the degree of wear of the support structure 16 may be determined by measuring the degree by which the voltages at output nodes 44a-c have decreased. As shown in FIG. 5, for example, if the voltage at output node 44c reaches a minimum threshold and falls below the voltage at output node 44g, the support structure 16 may be in a low-wear state. If the voltage at output node 44a, which is at a higher potential relative to the output node 44c, reaches a minimum threshold and falls below the voltage at output node 44g, the support structure 16 may be at a more critical open-circuit or high-wear state. In a similar fashion, the interface circuit 34 may also be preconfigured with thresholds to monitor for one or more of a normal state, a calibrated state, a shorted state, an end-of-life state, and the like.

Still referring to FIG. 5, once a threshold is exceeded, the corresponding comparator 46 may enable a respective LED 48 to illuminate and indicate to an operator or inspector of the respective operational state. For example, if the output voltage signal at the output node 44b falls below the threshold of the output voltage signal at output node 44g, the corresponding LED 48 may illuminate in red to indicate or warn that the support structure 16 is in an end-of-life state. The interface circuit 34 may optionally or additionally provide an audible alarm 50, such as a buzzer, ringer, or the like, that is further enabled by the associated comparator 46 so as to call attention to the monitoring system 24. Alternatively, the interface circuit 34 may further include a microcontroller configured to manage the illumination of one or more LEDs 48 based on the output signals, transmit alert notifications to a mobile device, display alert notifications at a monitor of a remote monitoring station, and the like. In still further modifications, the comparators 46 of FIG. 3 may further be configured to provide one or more control signals to the controller 22 of the elevator system 10 so as to, for instance, temporarily cease operation of the elevator system 10 in response to a detected fault or when a threshold has been exceeded. The control signals may be transmitted using discrete signals, serial communication, controller area network (CAN) bus, or any other suitable communication means. Alternatively, the interface circuit 34 may be configured to control a state of one or more relays of, for example an elevator safety chain, based on and/or in response to the output signals provided by the comparators 46. In such a way, the interface circuit 34 may communicate the operational state to, for example a controller 22, of the elevator system 10.

Figure 6:
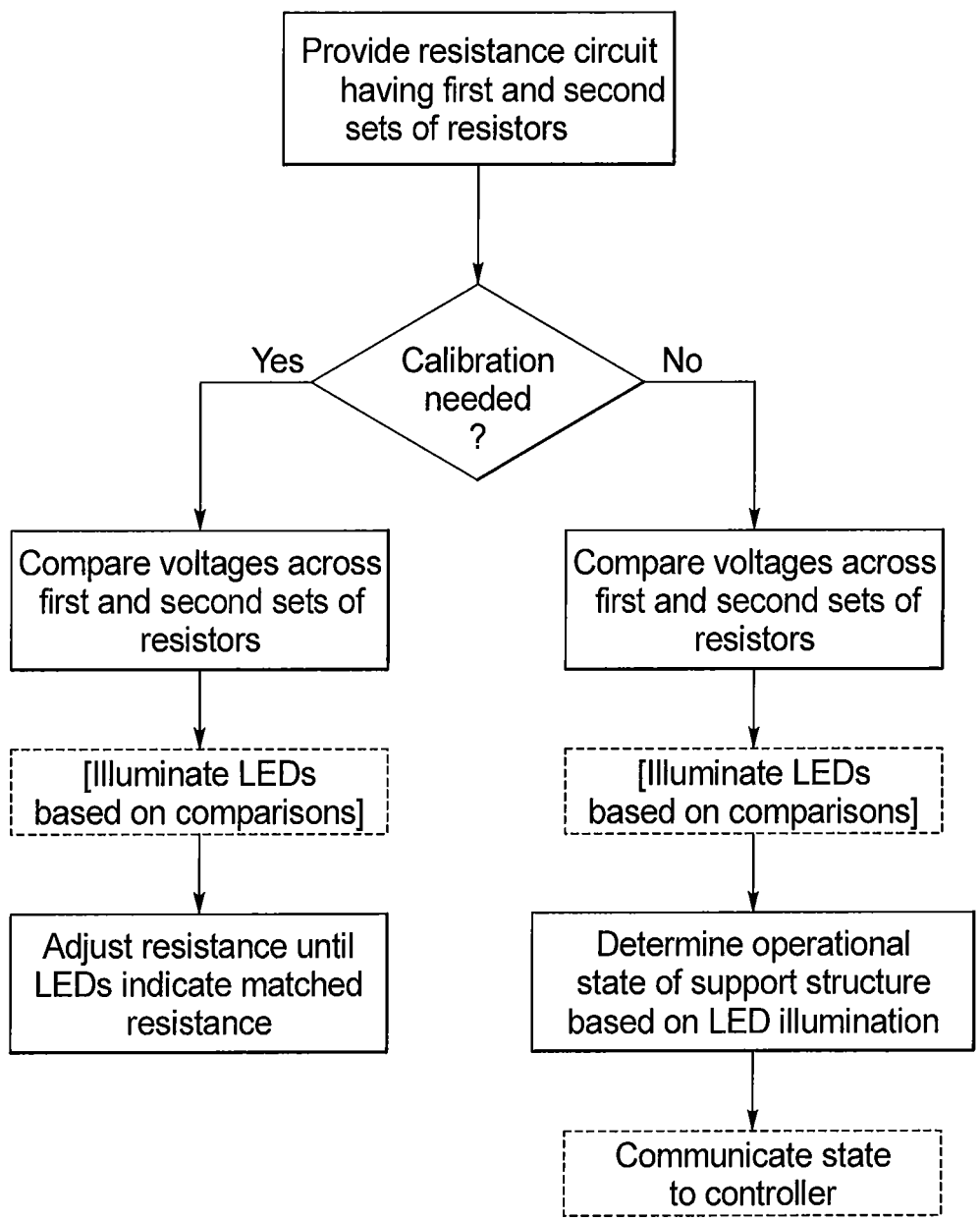
FIG. 6 is a diagrammatic view of a method for monitoring a support structure of an elevator system and a method for calibrating a resistance-based inspection system.

Turning now to FIG. 6, a flow diagram illustrating an exemplary method for monitoring a support structure 16 of an elevator system 10 as well as a method for calibrating a monitoring system 24 is provided. As an initial step, both methods may provide a resistance circuit 32 having a first set of resistors 40 and a second set of resistors 42 coupled to the support structure 16. In an optional step, an interface circuit 34 having a plurality of comparators 46 for comparing the voltages across the respective resistors 40, 44 may also be provided. An additional step may determine if calibration is needed, for example, if the support structure 16 is newly installed, if the support structure 16 has been recently replaced, or the like. If calibration is needed, one or more voltages across the first set of resistors 40 may be compared with a voltage across the second set of resistors 42 so as to determine the degree by which the electrical load or effective resistance of the support structure 16 matches the resistance of the second set of resistors 42. With respect to the arrangement of FIG. 5, for example, each of the output voltage signals at output nodes 44e-d may be compared with the reference voltage signal at output node 44g. If the reference voltage signal at output node 44g is greater than the output voltage signal at output node 44d or less than the output voltage signal at output node 44e, one or more LEDs 48 may be illuminated to indicate that adjustment of the second set of resistors 42 is needed. For example, if the voltage at output node 44g is greater than the voltage at output node 44d, a first LED 48 corresponding to the third threshold in FIG. 5 may illuminate in green while a second LED 48 corresponding to the fourth threshold in FIG. 5 may be completely off or illuminated in a different color. Alternatively, if the voltage at output node 44g is less than the voltage at output node 44e, the first LED 48 may be completely off or illuminated in a different color while the second LED 48 is illuminated in green. If the resistance of the second set of resistors 42 sufficiently matches the effective resistance of the support structure 16, and if the voltage at output node 44g is measured to be between the upper and lower limits of the voltages at output nodes 44d-e, respectively, both first and second LEDs 48 may be illuminated in green so as to indicate a successful calibration. In such a way, the resistance of the second set of resistors 42 may enable incremental adjustments of the second set of resistors 42 until both first and second LEDs 48 illuminate in green and indicate that the effective resistance of the support structure 16 is matched.

Once calibration is complete, or if calibration is not needed, the method for monitoring a support structure in FIG. 6 may also include a step of comparing one or more voltages across the first set of resistors 40 with a voltage across the second set of resistors 42. This is so as to determine the degree by which the effective resistance of the support structure 16 has diverged from the resistance initially matched by the second set of resistors 42 during calibration. Referring to the arrangement of FIG. 5, for example, each of the output voltage signals at output nodes 44a-f may be compared with the reference voltage signal at output node 44g. If any of the voltages at output nodes 44a-f rises above or falls below the reference voltage signal according to the respective thresholds as provided in FIG. 5, one or more LEDs 48 may be illuminated to indicate the operational state of the support structure 16 corresponding to the exceeded thresholds. For example, if the voltage at output node 44f is greater than the voltage at output node 44g, one or more LEDs 48 corresponding to the first threshold of FIG. 5 may be illuminated in red to indicate a shorted state, or when one or more tension members 26 of the support structure 16 are improperly in contact with one another. Accordingly, the immediate wear condition or operational state of the support structure 16 may be determined based on the continuous feedback provided by the illuminated LEDs 48.

Based on the foregoing, it can be seen that the present disclosure may provide a system and method for monitoring support structures of an elevator system with minimal complexity and more cost-effective implementations. The present disclosure may also provide continuous monitoring of support structures and enable immediate responses to detected fault conditions. Furthermore, the present disclosure provides a system and method which allows for easier and more accurate calibrations thereof.

While only certain embodiments have been set forth, alternatives and modifications will be apparent from the above description to those skilled in the art. These and other alternatives are considered equivalents and within the spirit and scope of this disclosure.

What is claimed is:

1. A monitoring system for a tensile support structure, comprising:
   a voltage input node to supply a voltage, the voltage applied to the tensile support structure;
   a resistance circuit connected to an effective resistance of the tensile support structure, the resistance circuit having a first set of resistors and a second set of resistors, the second set of resistors being coupled to the voltage input and configured to provide a reference voltage;
   the first set of resistors including at least two resistors in series and coupled to the voltage input, the at least two resistors in series being in parallel with the effective resistance of the tensile support structure; and
   an interface circuit directly coupled to the resistance circuit and having two or more comparators, each comparator being configured to directly compare a voltage across at least one of the at least two resistors with the reference voltage and generate an output signal corresponding to the comparison, the interface circuit being configured to monitor the effective resistance of the tensile support structure based on the output signals.

2. The monitoring system of claim 1, wherein the interface circuit is configured to continuously or intermittently monitor the effective resistance of the tensile support structure based on the output signals.

3. The monitoring system of claim 1, wherein at least one of the second set of resistors is adjustable so as to as approximate the effective resistance of the tensile support structure during calibration.

4. The monitoring system of claim 1, wherein a plurality of the second set of resistors is adjustable and configured in series such that the maximum resistance of each resistor is successively decreased.

5. The monitoring system of claim 1, wherein the resistance of each of the second set of resistors is different and enabled via a dual in-line package (DIP) switch.

6. The monitoring system of claim 5, wherein the DIP switches may be sealed upon calibration.

7. The monitoring system of claim 1, wherein the interface circuit is configured to control a relay based on the output signals.

8. The monitoring system of claim 1, wherein the resistance circuit further includes at least one temperature-dependent resistor having a variable resistance that is dependent on temperature.

9. The monitoring system of claim 1, wherein the interface circuit includes one or more light emitting diodes (LEDs) configured to receive the output signals and indicate one or more operational states of the tensile support structure based on the output signals.

10. The monitoring system of claim 9, wherein each operational state is indicative of the tensile support structure being in at least one of a shorted state, a normal state, a low-wear state, a high-wear state, an end-of-life state, and an open-circuit state.

11. A method for calibrating a resistance-based monitoring system for a tensile support structure, the method comprising:
    providing a resistance circuit connected to an effective resistance of the tensile support structure, the resistance circuit having a first set of resistors and a second set of resistors disposed at least partially in parallel to the tensile support structure, the first set of resistors including at least two resistors in series and coupled to a voltage input, the at least two resistors in series being in parallel with the effective resistance of the tensile support structure;
    generating a reference voltage across the second set of resistors;
    comparing a voltage across at least one of the first set of resistors directly with the reference voltage; and
    adjusting the reference voltage until an effective resistance of the tensile support structure is substantially matched by the resistance circuit:
    wherein the comparing includes providing two or more comparators coupled to the resistance circuit, each comparator being configured to directly compare a voltage across at least one of the first set of resistors with the reference voltage and generate an output signal corresponding to the comparison; and
    adjusting the resistance of the second set of resistors until the output signals indicate that the effective resistance of the tensile support structure is substantially matched by the resistance circuit.

12. The method of claim 11 further comprising:
providing one or more light emitting diodes (LEDs) coupled to the comparators, each LED being configured to receive the output signals and illuminate based on the comparisons; and
adjusting the resistance of the second set of resistors until an illumination of the LEDs indicates that the effective resistance of the tensile support structure is substantially matched by the resistance circuit.

13. The method of claim 11, wherein each of the second set of resistors is connected in series and configured with a different maximum resistance being enabled via a dual in-line package (DIP) switch, each DIP switch being successively enabled or disabled until the effective resistance of the tensile support structure is substantially matched.

14. The method of claim 13 further comprising sealing the second set of resistors once the effective resistance of the tensile support structure is substantially matched.

15. A method for monitoring a tensile support structure, comprising:
providing a resistance circuit connected to an effective resistance of the tensile support structure, the resistance circuit having a first set of resistors and a second set of resistors disposed at least partially in parallel to the tensile support structure, -the first set of resistors including at least two resistors in series and coupled to a voltage input, the at least two resistors in series being in parallel with the effective resistance of the tensile support structure;
generating a reference voltage across the second set of resistors, the reference voltage corresponding to an initial effective resistance of the tensile support structure;
directly comparing a voltage across at least one of the first set of resistors with the reference voltage; and
determining at least one operational state of the tensile support structure based on the comparisons:
providing two or more comparators coupled to the resistance circuit, each comparator being configured to directly compare a voltage across at least one of the first set of resistors with the reference voltage and generate an output signal corresponding to the comparison;
providing one or more light emitting diodes (LEDs) coupled to the comparators, each LED being configured to receive the output signals and illuminate based on the comparisons; and
determining at least one operational state of the tensile support structure based on an illumination of the LEDs.

16. The method of claim 15, wherein the resistance of each of the second set of resistors is adjustable and enabled via a dual in-line package (DIP) switch.

17. The method of claim 15, wherein each operational state is indicative of the tensile support structure being in at least one of a shorted state, a normal state, a low-wear state, a high-wear state, an end-of-life state, and an open-circuit state.

* * * * *